United States Patent [19]
Zook et al.

[11] 3,971,256
[45] July 27, 1976

[54] METEOROID CAPTURE CELL CONSTRUCTION

[75] Inventors: Herbert A. Zook; Richard W. High, both of Houston, Tex.

[73] Assignee: The United States of America as represented by the Administrator of the National Aeronautics and Space Administration, Washington, D.C.

[22] Filed: Mar. 5, 1974

[21] Appl. No.: 448,320

[52] U.S. Cl............................ 73/425.2; 73/170 R; 73/432 R
[51] Int. Cl.².......................................... G01N 1/00
[58] Field of Search........... 73/11, 12, 170 R, 425.2, 73/432 R, 432 PS, 425, 28

[56] References Cited
UNITED STATES PATENTS

| | | | |
|---|---|---|---|
| 3,446,068 | 5/1969 | Slattery et al...................... | 73/12 X |
| 3,678,759 | 7/1972 | Schneeberger.................. | 73/432 PS |
| 3,842,656 | 10/1974 | Di Battista.................... | 73/432 PS X |

*Primary Examiner*—Richard C. Queisser
*Assistant Examiner*—John S. Appleman
*Attorney, Agent, or Firm*—Carl O. McClenny; John R. Manning; Marvin F. Matthews

[57] ABSTRACT

A thin membrane covering the open side of a meteoroid capture cell causes an impacting meteoroid to disintegrate as it penetrates the membrane. The capture cell then contains and holds the meteoroid particles for later analysis.

3 Claims, 3 Drawing Figures a.

b.

U.S. Patent   July 27, 1976   3,971,256
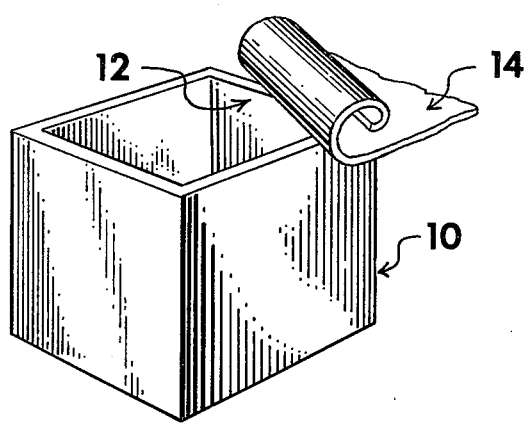
Fig 1
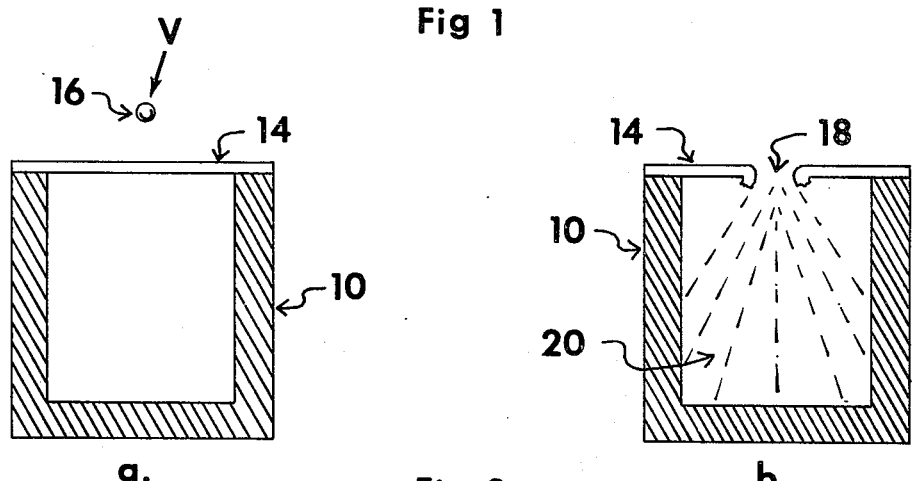
a.   Fig 2   b.
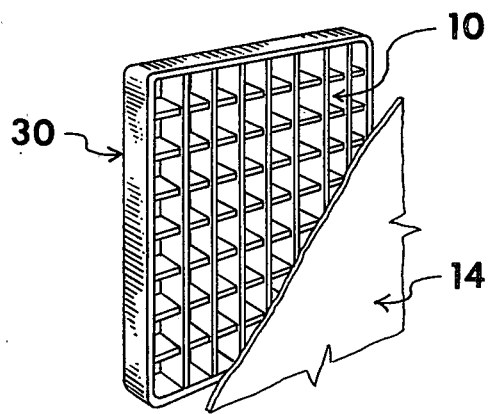
Fig 3

METEOROID CAPTURE CELL CONSTRUCTION

ORIGIN OF THE INVENTION

The invention described herein was made by employees of the U.S. Government and may be manufactured and used by or for the Government of the United States of America for governmental purposes without the payment of any royalties thereon or therefor.

BACKGROUND OF THE INVENTION

The invention relates to meteoroid capturing devices and is directed more particularly to one employing a cavity (or cell) covered by a thin membrane.

There are three ways in which meteoroids have been studied and analyzed in the past. One way has been to analyze meteorites, i.e., the remnants that one finds on the ground, of meteoroids which have passed through the atmosphere. There are reasons to believe, however, that only a special class of meteoroids do not burn completely upon their entry into the atmosphere, thereby leaving a remnant (meteorite) which can be analyzed. Hence, the analysis of meteorites may give a distorted view of the general composition of meteoroids. Another technique is to analyze the spectra of meteor trails, the fiery trail made by an incoming meteoroid. However, this technique is presently beset with considerable difficulty and uncertainty.

A third technique, developed relatively recently, works as follows: A set of meteoroid interaction surfaces, shaped somewhat like a semi-open venetian blind, is launched into space. Behind the interaction surfaces, a strong electric field is applied to accelerate positive ions toward a current measuring device. When a meteoroid strikes one of the interaction surfaces, part of it is spewed off as an ionized vapor. The positive ions in this ionized vapor are then accelerated toward the charge collector. The ratio of electric charge to mass of the various species of positive ions determines their respective times of arrival relative to the detection of electrons near the interaction surfaces. This technique suffers from problems similar to those encountered in analyzing meteor trails. Namely, the probability of ionization of the various species of elements under hypervelocity impact conditions is not well known and therefore the original meteoroid composition cannot be accurately determined.

SUMMARY OF THE INVENTION

Meteoroids are captured in the following manner: Arrays of cube or other shaped cells of very pure material are constructed for deployment from a spacecraft. One side of the cell is left open over which a thin membrane, preferably of the same material as the cells, is affixed. A meteoroid then strikes the thin membrane and enters the cell. Because of the very high velocity of the meteoroid, the thin membrane causes the meteoroid to completely shatter or disintegrate. The membrane is, however, thin enough to allow penetration of all the meteoroid particles which lie in the mass range for which the cell is designed. The rest of the cell is manufactured thick enough to contain the high velocity remnants of the meteoroid as well as most of the vapor that may be created due to impact heating. The contents of the cell are later analyzed for element and chemical content.

Meteoroids collected and analyzed in this fashion should not suffer from the same selection effects of picking out a specialized class as do meteorite studies, meteor studies, or impact ionization studies. The technique taught by this invention enables one to bring the meteoroid into the lab for whatever analysis is desired, whereas analysis of meteors, for example, can only be done spectroscopically (except for very large bolides where high-flying airplanes may take samples of the air that includes some meteoritic material).

It is an object of the invention to provide a meteoroid capture cell, for capturing and containing meteoroids, wherein minimum contamination of the meteoroid particles by the cell is achieved.

It is another object of the invention to provide a membrane, or cell covering, which will cause disintegration of an impacting meteoroid while allowing a large percentage of the selected particles to penetrate the membrane and be captured within the cells.

It is a further object of the invention to provide a cell wall of a thickness and material which will provide sufficient strength to contain or hold a disintegrating meteoroid while minimizing the cell weight.

It is still another object of the invention to provide a meteoroid capture cell which will withstand all the environmental conditions to which a spacecraft may be exposed.

Other objects and advantages of the invention will become apparent from the description and the drawing of a meteoroid capture cell embodying the invention.

BRIEF DESCRIPTION OF THE DRAWINGS

FIG. 1 is an isometric drawing of a single meteoroid capture cell with its membrane displaced.

FIG. 2 illustrates the process of meteoroid breakup and capture by a cell.

FIG. 3 illustrates an array of capture cells.

DESCRIPTION OF THE PREFERRED EMBODIMENT

Referring now to FIG. 1, reference numeral 10 designates a meteoroid capture having an open side 12. A thin membrane 14, preferably of the same material as the capture cell 10, covers the open side 12 of the capture cell 10. When a meteoroid of the preferred size range impacts the membrane 14, two reactions occur. First, the membrane 14 is penetrated by the meteoroid, and second, the meteoroid disintegrates under the collision-induced shock pressure. The particles of the disintegrated meteoroid are thus captured within the cavity of the capture cell 10. A relatively small portion of the impacting meteoroid is back-splattered from the membrane 14 and is lost. FIG. 2 illustrates the process of meteoroid capture by a cell wherein a meteoroid 16 having a velocity v strikes the membrane 14, whereupon the membrane 14 is penetrated at 18 and the meteoroid 16 shatters upon impact. The meteoroid particles 20 are embedded in the inner walls of the capture cell 10 where they remain until removed for analysis.

FIG. 3 depicts an array 30 of capture cells 10 having a common membrane 14.

Meteoroids are of sizes ranging from less than $10^{-12}$ gm to approximately $10^{+12}$ gm (above which size they may be called asteroids or comets). Although the invention described does not depend upon meteoroid size, the physical size of the meteoroid capturing device will depend upon the size meteoroid one desires to capture. There are some advantages, in terms of size and cost, to try to capture fairly small ($\sim 10^{-6}$ gm)

meteoroids rather than larger ones. Although the invention is not restricted to capturing small meteoroids, present design efforts are directed toward trying to capture meteoroids in the mass range $10^{-7}$ to $10^{-4}$ gm.

Meteoroids strike the upper atmosphere of the earth with velocities ranging from 11 to 72 km/sec with an average velocity of about 19 km/sec. The impacting velocities relative to an earth-orbiting or to an interplanetary spacecraft would be distributed differently from those entering the upper atmosphere. However, nearly all of the meteoroids striking a spacecraft, regardless of its trajectory, would have velocities in the hypervelocity range. The term hypervelocity is defined to be that velocity (about 3 or 4 km/sec) above which a meteoroid will completely shatter upon striking another object.

Various techniques for chemical analysis of the meteoroid particles may be used, such as neutron activation, electron microprobe, emission spectroscopy, and so on.

As an example of cell size, suppose one wished to capture meteoroids in the mass range of $10^{-7}$ to $10^{-4}$ gm. With an assumed meteoroid density of 2 gm/cm$^3$, the corresponding projectile diameters would range from about 50 to 500 microns. A 10 micron thick membrane (thickness is somewhat dependent on membrane composition) would allow penetration by practically all of a 50 micron projectile. It would also break up the 500 micron projectile sufficiently so that the rest of the cell being used as a catcher need not be unduly thick and heavy to contain the debris. Membrane and cell wall thickness should be optimized for the meteoroid mass of particular interest.

Because meteoroids do not arrive very often, many cells are required to construct a practical experiment. To have a 65% probability of capturing a $10^{-6}$ gm or larger meteoroid, one should expose about 0.56 square meters of collecting area for 1 year. More precisely, any combination of area-time products that gives 0.56 m$^2$ — years of experiment exposure to space will produce a reasonable probability of capturing a meteoroid that has at least $10^{-6}$ gm mass. Hence, for most experimental uses of the design described above, a very large number of cells are required. One prototype (see FIG. 3) utilized an "egg crate" design having individual cells about 6.4 mm on a side with 64 cells in each unit of the design. The "unit" was designed to be one of many to be structurally held in a lightweight frame. The container was made of 1.27 mm 1,100 aluminum having cell walls of 0.76 mm 1,100 aluminum. The cells were lined with 0.9999 purity aluminum foil and covered with a membrane of the same material. A later prototype was made with high-purity polyethylene cells. Polyethylene or other synthetic material cells are preferred over aluminum or other metals for at least two reasons: (1) Polyethylene or other synthetic materials can be obtained in extremely pure form; and, (2) if a metal is used, that metal and its associated impurities usually cannot easily be separated from the meteoroid debris in the analysis.

The procedure involved in operating the invention is to expose an array of cells to the space environment so that meteoroids can strike the membranes covering the cells. Before injection into and deployment in space, the cells must be packaged in some suitable manner which does not require too much weight and volume. This is also true upon return from space. They could be initially rolled up, for example, or folded accordian-like and then deployed by unrolling or unfolding. It is also possible that the transport volume could be further decreased by making the individual cells collapsible.

We claim:
1. A meteoroid capture cell comprising:
   a. A housing for receiving and restraining particles from shattered meteoroids of a pre-selected size class, said housing being constructed entirely of one chemical substance having a purity of at least 0.9999 and having one open side for receiving therethrough said particles and wherein the thickness of said housing substance is resistant to complete penetration by said particles; and,
   b. A membrane comprised of the same chemical substance as said housing affixed to and covering the open side of said housing wherein the thickness of said membrane is responsive to penetration by a meteoroid of said pre-selected size class striking said membrane while causing complete shattering of said meteoroid as said meteoroid penetrates said membrane.

2. The capture cell of claim 1 wherein said chemical substance is polyethylene.

3. The capture cell of claim 1 wherein said chemical substance is aluminum, the thickness of said housing walls is approximately 1.27 mm and the thickness of said membrane is approximately 0.025 mm.

* * * * *